United States Patent [19]

Williams et al.

[11] Patent Number: 5,186,926
[45] Date of Patent: Feb. 16, 1993

[54] FLAVOR FOR PEROXIDE-BICARBONATE ORAL COMPOSITIONS

[75] Inventors: David R. Williams, Monroe; Christine W. Ryles, Milford, both of Conn.

[73] Assignee: Chesebrough-Pond's USA Co., Division of Conopco, Inc., Greenwich, Conn.

[21] Appl. No.: 816,992

[22] Filed: Jan. 3, 1992

Related U.S. Application Data

[62] Division of Ser. No. 719,871, Jun. 24, 1991, Pat. No. 5,085,853.

[51] Int. Cl.$^5$ .................. A61K 7/16; A61K 7/20; A61K 33/40
[52] U.S. Cl. .................. 424/53; 424/49; 424/616; 424/717
[58] Field of Search .................. 424/49, 53, 616, 717

[56] References Cited

U.S. PATENT DOCUMENTS

| | | | |
|---|---|---|---|
| 3,577,521 | 5/1971 | Scheller et al. | 424/55 |
| 3,729,553 | 4/1973 | Gold et al. | 424/44 |
| 3,937,803 | 2/1976 | Delaney et al. | 424/49 |
| 4,132,770 | 1/1979 | Barth | 424/49 |
| 4,487,757 | 12/1984 | Kiozpeoplou | 424/7.1 |
| 4,528,180 | 7/1985 | Schaeffer | 424/52 |
| 4,537,778 | 8/1985 | Clipper et al. | 424/53 |
| 4,837,008 | 6/1989 | Rudy et al. | 424/53 |
| 4,849,213 | 7/1989 | Schaeffer | 424/53 |
| 4,925,655 | 5/1990 | Smiga et al. | 424/52 |
| 4,980,152 | 12/1990 | Frazier et al. | 424/53 |
| 5,059,417 | 10/1991 | Williams et al. | 424/53 |
| 5,085,853 | 2/1992 | Williams et al. | 424/53 |

FOREIGN PATENT DOCUMENTS

| | | | |
|---|---|---|---|
| 1136990 | 12/1982 | Canada | 424/717 |
| 944506 | 4/1949 | France . | |
| 56-59703 | 5/1981 | Japan | 424/717 |
| 3-279321 | 12/1991 | Japan | 424/717 |

OTHER PUBLICATIONS

Periodontics and Oral Hygiene, Keyes et al, Jan. 1978, pp. 51-56.

Primary Examiner—Shep K. Rose
Attorney, Agent, or Firm—Milton L. Honig

[57] ABSTRACT

An oral composition is provided having a first peroxide-containing component and a second bicarbonate-containing component. The first component has a flavor which is reactively incompatible with bicarbonate salts while the second component has a flavor which is reactively compatible with the bicarbonate.

8 Claims, No Drawings ics and Oral Hygiene", January, 1978, pages 51-56. Unfortunately, formulations based on the Keyes technology are particularly prone to decomposition.

Several approaches have been reported to overcome difficulties presented by such combination of ingredients. U.S. Pat. No. 3,577,521 (Scheller) discloses use of acid salts in combination with alcohol-silica gels to obtain a foaming storage-stable toothpaste of peroxide-bicarbonate.

U.S. Pat. No. 4,837,008 (Rudy et al) overcomes the problem through a non-aqueous dentifrice wherein an inorganic peroxide and/or bicarbonate is coated with a water-soluble barrier which is insoluble in the dentifrice vehicle.

Physical isolation of the peroxide from co-reactive ingredients into separate compartments has been another approach to the problem. U.S. Pat. No. 4,849,213 and U.S. Pat. No. 4,528,180, both to Schaeffer, disclose a dual-compartment package containing respective peroxide gel and bicarbonate paste components. U.S. Pat. No. 4,487,757 (Kiozpeoplou) discloses a toothpaste that physically segregates sodium bicarbonate from acidic ingredients to prevent contact therebetween prior to usage.

U.S. Pat. No. 4,537,778 (Clipper) describes hydrogen peroxide oral compositions and the problems of flavors being destroyed through oxidation. Certain flavors including methyl salicylate, menthol, cinnamic aldehyde and clove oil were all reported to be satisfactorily stable in the peroxide composition. In contrast to the aforementioned components that produce wintergreen, peppermint and spearmint flavors, the fruity and other minty flavors were found to decompose. For bicarbonate toothpastes it is known through U.S. Pat. No. 3,937,803 (Delaney et al) to include therewith peppermint flavors.

From all of the aforementioned art, it is apparent that hydrogen peroxide and bicarbonate compositions should be formulated as simply as possible to minimize potential interactions between the peroxide and bicarbonate and each of these with any other remaining ingredients.

Although great progress has been made, flavors still remain a problem. For instance, methyl salicylate induces decomposition of bicarbonate. Liberated carbon dioxide gas then causes expansion of tubes containing the dentifrice. On the other hand, wintergreen flavor which is a combination of methyl salicylate and menthol causes problems when incorporated into a hydrogen peroxide composition. Menthol is prone to oxidation, notwithstanding teachings to the contrary in U.S. Pat. No. 4,537,778.

Accordingly, it is an object of the present invention to provide a peroxide-bicarbonate dual component oral composition which can be formulated with a relatively wide range of flavorants.

A further object of the present invention is to provide a peroxide-bicarbonate dual component oral composition which does not degrade flavor nor conversely is decomposed by the flavor even after extended storage periods.

These and other objects of the present invention will become more readily apparent upon consideration of the more detailed description and examples which follow.

SUMMARY OF THE INVENTION

An oral composition comprising:
(A) a first component comprising:
(i) a peroxygen compound present in an amount from about 0.1 to about 10% by weight of the first component;
(ii) a first flavor agent which is reactively incompatible with bicarbonate salts, the first flavor agent being present in an effective amount to impart a flavor taste;
(B) a second component comprising:
(i) a bicarbonate salt present in an amount from about 0.5 to about 80% by weight of the second component;
(ii) a second flavor agent which is reactively compatible with the bicarbonate salt, the second flavor agent being present in an effective amount to impart a flavor taste, the components being held in separate areas of a container for the oral composition, and relative weight amounts of the first and second components ranging from about 2:1 to 1:20.

Methyl salicylate is the preferred first flavor agent. Menthol may be formulated with the bicarbonate component as the second flavor agent. Advantageously, the relative weight ratio of the first to second flavor agent should range from about 1:1 to about 1:15, with a ratio of about 1:2 being optimum.

DETAILED DESCRIPTION

A practical means has been discovered for flavoring a two-component peroxide-bicarbonate oral composition. Experiments have determined that the bicarbonate portion is quite reactive towards flavors such as cinnamic aldehyde, eugenol (clove oil) and methyl salicylate. Gas evolution or at least browning of the bicarbonate component occurs when the aforementioned flavors are combined therewith. Now it has, however, been determined that menthol is stable with respect to the bicarbonate. On the other hand, menthol has some slight susceptibility to oxidation and preferably is not formulated with the peroxygen compound component.

Accordingly, in one aspect of the invention, the peroxide component will have a first flavor agent which is reactively incompatible with bicarbonate salts. The first flavor agent may be selected from clove oil, cinnamic aldehyde, methyl salicylate and combinations thereof. In a second aspect of the invention, the bicarbonate portion will incorporate a second flavor agent which is reactively compatible with bicarbonate. Menthol is illustrative of this second flavor agent.

Another aspect of the invention is the importance of controlling relative weight ratios of first to second flavor agents. Thus it is advantageous to limit the first to second flavor agents to weight ratios of from about 2:1 to about 1:20, preferably from about 1:1 to about 1:15, optimally from about 1:1 to about 1:3.

Oral compositions of the present invention may be in the form of either a toothpaste, liquid rinse such as a mouthwash or in tablet form. Relative weight amounts of the first peroxygen-containing component to the second bicarbonate-containing component will range from about 1:2 to 2:1, preferably about 1:1. Each component may be kept isolated in a separate compartment of a dispenser. Advantageously, the dispenser will simultaneously deliver approximately equal amounts of each component through an orifice at whose end the separate components may intermingle. Suitable for this purpose are dual-compartment packages such as described in the Schaeffer patents, U.S. Pat. No. 4,528,180 and U.S. Pat. No. 4,849,213. Most preferred is where the peroxygen component is in the form of a transparent gel and the bicarbonate component is in the form of an opaque paste. These preferred embodiments will more fully be illustrated below.

The gel component notably will contain a water-soluble peroxygen compound such as an alkali metal perborate, percarbonate, urea peroxide, persilicate, perphosphate or hydrogen peroxide. Most suitable for this invention is hydrogen peroxide. Amounts of the peroxygen compound may range from about 0.1 to about 10% by weight of the gel component. In terms of active weight hydrogen peroxide, the amount will range from about 0.5% to about 3%, preferably from about 0.8% to about 1.8%, optimally between about 1% and 1.5% by weight of the gel component.

Water will be present in the gel in amounts ranging from about 20% to about 70%, preferably between about 30 to 55%, optimally between 30 to 40% by weight of the gel component.

An effective amount of thickening agent in combination with water will be necessary for solidifying the gel component. Cross-linked acrylic polymers may be utilized for this purpose. However, the most preferred structurants are the polyoxyethylene-polyoxypropylene copolymers having a hydrophobic portion, represented by $(C_3H_6O)$, having a molecular weight range from about 2,750 to 4,000 and a hydrophilic portion, represented by $(C_2H_4O)$ constituting about 70-80% of the weight of the copolymer.

Commercially, the copolymers are available from the BASF Corporation under the trademark, Pluronic F88, F99, F108 and F127. Most preferred is Pluronic F127 (more commonly described by its CTFA name, Poloxamer 407) which has a molecular weight ranging from about 10,000 to 15,000, and containing about 70% of the hydrophilic polyoxyethylene moiety. Amounts of the copolymer can range anywhere from 18-25% by weight, preferably between 19 and 24%. Poloxamers are particularly suitable for this invention because of their wide pH tolerance, high compatibility with hydrogen peroxide and unique gel properties.

Advantageously, glycerol should also be present in the gel component in an amount from about 15 to 60%, preferably in an amount greater than 30% but less than 50%, optimally between about 35 to 45% by weight of the gel component.

A low pH, preferably a pH no higher than about 3, optimally less than 3.0, should be maintained for the gel component. Acidification is best accomplished through the use of a phosphorus-based inorganic or organic acid.

The second component of the oral compositions of the invention will preferably be a bicarbonate-containing opaque paste. Elements of this component are outlined below.

Advantageously, the bicarbonate will be the salt of an alkali metal such as sodium or potassium. Normally, the bicarbonate is included in the composition in an amount sufficient to provide a neutral and basic pH when the composition is contacted with water, preferably a pH of from about 7.0 to about 9.5, most preferably about 8.0 to 9.0. Typically, the concentration will range from about 0.5 to about 80%, preferably from about 5 to 50%, optimally between about 8 and 20% by weight of the second component.

A humectant and water system will normally be included. Humectants are usually polyols which, for example, may include glycerol, sorbitol, propylene glycol, lactitol, xylitol, polypropylene glycol, polyethylene glycol, hydrogenated corn syrup and mixtures thereof. Generally the amount of humectant will range from about 25 to 90%, preferably from about 40 to 70% by weight. Particularly preferred is a liquid mixture of 3 to 30% water, 0 to 80% glycerol and/or 20 to 80% sorbitol.

A natural or synthetic thickening agent may be present in an amount from about 0.1 to about 10%, preferably about 0.5 to 5% by weight of the second component may be present. Thickeners may include hydroxypropyl methylcellulose, hydroxyethyl cellulose, sodium carboxymethyl cellulose, xanthan gum, tragacanth gum, karaya gum, arabic gum, Irish moss, starch, alginates and carrageenans.

Surfactants are normally also included in the second component of the oral composition of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

An abrasive in addition to the bicarbonate will normally be included in the second component paste. Abrasives may be selected from water-insoluble alkali or alkaline earth metal salts of metaphosphate (IMP), calcium carbonate, aluminate and silicate. Especially preferred are silica, dicalcium phosphate and calcium carbonate. Amounts of the abrasive will range from about 5 to about 80% by weight of the second component.

Tartar control agents may be incorporated into compositions of this invention, especially effective will be agents containing phosphorous. Inorganic phosphorous tartar control agents may include any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as tartar control agents include polyphosphonates such as disodium ethane-1-hydroxy-1, 1-diphosphonate (EHDP), methanediphosphonic acid, and 2-phosphonobutane-1,2,4-tricarboxylic acid.

For anti-caries protection, a source of fluoride ion will normally be present in the second component of the oral composition. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.2 to 1% by weight of the second component.

Sweetening agents such as saccharin, sodium cyclamate, aspartame, sucrose and the like may be included at levels from about 0.1 to 5% by weight.

Other additives may also be incorporated into the oral compositions including preservatives, silicones, other synthetic or natural polymers such as Gantrez S-97, and anti-gingivitis actives.

The following examples will more fully illustrate the embodiments of this invention. All parts, percentages and proportions referred to herein and in the appended claims are by weight of the total composition unless otherwise stated.

EXAMPLE 1

Typical of the present invention are paste and gel components whose formulations are detailed under Tables I and II.

TABLE I

Bicarbonate Paste Component

| Ingredient | Wt. % |
|---|---|
| Polyol II (sorbitol and other sugars) | 48.710 |
| Syloid 63XX (abrasive silica) | 15.000 |
| Sodium Bicarbonate | 10.000 |
| PEG 32 (polyethylene glycol) | 5.000 |
| Sylox 15x (thickening silica) | 4.600 |
| Sodium Lauryl Sulfate | 2.980 |
| SD Alcohol 38B | 2.850 |
| Cellulose Gum | 0.800 |
| Menthol | 0.500 |
| Sodium Saccharin | 0.500 |
| Sodium Fluoride | 0.460 |
| Titanium Dioxide | 0.300 |
| Deionized water | Balance |

TABLE II

Peroxide Gel Component

| Ingredient | Wt. % |
|---|---|
| Pluronic F127 | 20.000 |
| Glycerin | 40.000 |
| Hydrogen Peroxide (35% food grade) | 4.285 |
| Methyl Salicylate | 0.500 |
| FD & C Blue | 0.005 |
| Phosphoric Acid (85% w/w) | 0.150 |
| Deionized water | Balance |

EXAMPLE 2

A series of stability experiments were conducted to evaluate the effect of methyl salicylate on a peroxide gel component.

The test employed was the Peroxide Stability/Stress Test (PSST). Samples were exposed to accelerated aging at a temperature of 95° C. over a 6-hour period. These aging conditions were found to have good correlation with 3-month storage stability testing at 105° F. Peroxide content of the gel was assayed by oxidizing potassium iodide to iodine and titrating with sodium thiosulphate on an auto-titrator fitted with a redox electrode.

Gel components having essentially the same ingredients as that identified under Table II of Example 1 were herein evaluated. Sample A was based on 1.5% hydrogen peroxide with 0.5% methyl salicylate. Sample B was a control identical to Sample A except without any methyl salicylate. The samples were first stored for the indicated period of time at 105° F. or at room temperature. Each of the samples was then rapidly aged at 95° C. for 6 hours prior to measuring residual peroxide content. Table III outlines the results.

TABLE III

Peroxide Stability Results

| | Sample A* | | | Sample B (Control)* | | |
|---|---|---|---|---|---|---|
| | None | 1-Mo. | 2-Mos. | None | 1-Mo. | 2-Mos. |
| Initial (H$_2$O$_2$ %) | 1.53 | 1.50 | 1.55 | 1.52 | 1.51 | 1.53 |
| After 6 Hours/95° C. (H$_2$O$_2$ %) | 1.33 | 1.21 | 1.25 | 1.34 | 1.14 | 1.28 |
| Recovery % | 86.93 | 80.67 | 81.00 | 88.16 | 75.20 | 84.00 |

*Aging storage period at 105° F.

Evident from Table III is that methyl salicylate did not destabilize the peroxide gel component, even after a 2-month accelerated storage and PSST Test.

Higher levels of hydrogen peroxide were also evaluated. Table IV lists the results of an evaluation comparing a 3% hydrogen peroxide gel identified as Sample C containing 0.5% methyl salicylate against a non-flavored control 3% hydrogen peroxide gel identified as Sample D.

TABLE IV

Peroxide Stability Results

| | Sample C | Sample D |
|---|---|---|
| Initial (H$_2$O$_2$ %) | 2.90 | 2.80 |
| After 6 Hours/95° C. (H$_2$O$_2$ %) | 2.57 | 2.46 |
| Recovery % | 88.62 | 87.50 |

Based on results listed in Table IV, it is noted that even at 3% hydrogen peroxide, the methyl salicylate is stable in the gel component.

EXAMPLE 3

A series of experiments were performed to evaluate compatibility of various flavors with the bicarbonate paste as outlined under Example 1. These experiments are listed in Table V.

TABLE V

Bicarbonate Stability Results

| Sample | Flavor Type | Compatibility |
|---|---|---|
| 1 | Cinnamic Aldehyde | Browned the white bicarbonate paste |
| 2 | Clove Oil (H and R Clove Mint) | Browned the white bicarbonate paste |
| 3 | Methyl Salicylate | Gaseous evolution in bicarbonate paste |
| 4 | Menthol | Good Stability |
| 5 | Spearmint | Turned instantly to bitter flavor when mixed with peroxide gel |

EXAMPLE 4

Hereunder are reported experiments which evaluate the taste benefits of separating methyl salicylate from menthol and optimum ratios for each of the flavor agents.

Taste evaluations were performed on a series of dentifrices formulated as shown under Example 1. Levels by % weight of menthol and methyl salicylate were varied in each of the dentifrice samples. A sensory panel of six persons was assembled to evaluate these samples. The panelists were instructed to brush with each dentifrice leaving at least one hour between brushings. Table VI lists the samples evaluated.

TABLE VI

Bicarbonate Paste/Peroxide Gel Toothpaste Taste Evaluation

| Dentifrice | Peroxide Gel % Me Sal | Peroxide Gel % Menthol | Bicarbonate Paste % Me Sal | Bicarbonate Paste % Menthol | Wt. Ratio Me Sal: Menthol |
|---|---|---|---|---|---|
| A | — | — | 0.5 | 1.1 | 1:2.2 |
| B | 0.5 | — | — | 1.1 | 1:2.2 |
| C | 3.3 | — | — | 1.1 | 3:1 |
| D | 2.2 | — | — | 1.1 | 2:1 |
| E | 0.55 | — | — | 1.1 | 1:2 |
| F | 0.11 | — | — | 1.1 | 1:10 |
| G | 1.24 | — | — | 0.41 | 3:1 |
| H | 1.1 | — | — | 0.55 | 2:1 |
| I | 0.55 | — | — | 1.1 | 1:2 |
| J | 0.15 | — | — | 1.5 | 1:10 |

Dentifrices A and B were compared to test taste performance when flavors were separated into different component phases. All six panelists preferred the overall flavor of sample B which contained the flavor in separate form over that of sample A. It was concluded that a unique differentiation of wintergreen and mint notes could be achieved through flavor separation in the two phases which was unachievable when both flavor components were combined only into the bicarbonate paste.

A second set of experiments (samples C through F) determined the preference for a variety of wintermint flavors based on methyl salicylate to menthol ratios at constant menthol content. At optimum menthol level (1.1%), samples C and D were found by the six panelists to be far too strong in methyl salicylate to be acceptable. Sample F at a 1:10 methyl salicylate to menthol ratio was found to be negligible in wintergreen flavor. Sample E provided the only acceptable wintermint flavor in this group.

A third objective of the test was to identify the preference for a variety of wintermint flavors based on menthol to methyl salicylate ratios at constant overall flavor dose. See results with respect to samples G through J. In this group, as methyl salicylate level declines, preference increases (see Table VII). The panel for this test was smaller (four members) and apparently showed a bias for mint likers over wintergreen flavors. The mean panel score identified preferences for the 1:10 and 1:2 ratios of methyl salicylate to menthol in separated phases while the 2:1 and 3:1 ratios moved into the dislike end of the scale.

TABLE VII

| Toothpaste | Attribute | Mean Panel Score |
|---|---|---|
| G | Wintergreen | 4.5 |
|  | Mint | 1.2 |
|  | Flavor Strength | 4.15 |
|  | Preference (like is low) | 3.3 |
| H | Wintergreen | 3.8 |
|  | Mint | 1.6 |
|  | Flavor Strength | 3.6 |
|  | Preference (like is low) | 3.1 |
| I | Wintergreen | 2.5 |
|  | Mint | 2.8 |
|  | Flavor Strength | 3.2 |
|  | Preference (like is low) | 2.5 |
| J | Wintergreen | 1.2 |
|  | Mint | 3.7 |
|  | Flavor Strength | 3.3 |
|  | Preference (like is low) | 1.9 |

Note on Sensory Scales

Flavor type, strength scores are optimum around score 3. Preference score 3 defines neither like nor dislike. Movement in either direction away from this score moves preference into the like or dislike area.

The foregoing description and Examples illustrate selected embodiments of the present invention. In light thereof, various modifications will be suggested to one skilled in the art, all of which are within the spirit and purview of this invention.

What is claimed is:

1. An oral mouthwash composition comprising:
   (A) a first component which is a liquid comprising:
      (i) a peroxygen compound present in an amount from about 0.1 to 10% by weight of the first component;
      (ii) a first flavor agent which is reactively incompatible with bicarbonate salts, said first flavor agent being present in an effective amount to impart a flavor taste;
   (B) a second component which is a liquid comprising:
      (i) a bicarbonate salt present in an amount from about 0.5 to about 80% by weight of the second component;
      (ii) a second flavor agent which is reactively compatible with said bicarbonate salt and different from the first flavor agent, said second flavor agent being present in an effective amount to impart a flavor taste, said components being held in separate compartments of a dual-compartment dispenser container for said oral composition, and relative amounts of aid first and second flavor agents ranging from about 2:1 to 1:20.

2. A composition according to claim 1, wherein aid first flavor agent is selected from the group consisting of methyl salicylate, cinnamic aldehyde, clove oil, and combinations thereof.

3. A composition according to claim 1, wherein said second flavor agent is menthol.

4. A composition according to claim 1, wherein said peroxygen compound is hydrogen peroxide present in an amount ranging from about 0.5 to about 5% by weight of the first component.

5. A composition according to claim 1, wherein the bicarbonate salt is sodium bicarbonate present in an amount from about 5% to about 20% by weight of the second component.

6. A composition according to claim 1, wherein said first flavor agent relative to said second flavor agent is present in a weight ratio of about 1:1 to about 1:15.

7. A composition according to claim 1, wherein said first flavor agent relative to said second flavor agent is present in a weight ratio of about 1:1 to about 1:3.

8. A composition according to claim 1, wherein said first flavor agent is methyl salicylate and said second flavor agent is menthol, said menthol being absent from said first component.

* * * * *